United States Patent [19]
Caldwell et al.

[11] Patent Number: 4,966,907
[45] Date of Patent: Oct. 30, 1990

[54] 6-SUBSTITUTED 5-HYDROXY-2,3-DIHYDROBENZOFURANS AS INHIBITORS OF LEUKOTRIENE BIOSYNTHESIS

[75] Inventors: Charles G. Caldwell, Scotch Plains; Milton L. Hammond, Somerville; Ihor E. Kopka, Newark, all of N.J.; Stanley H. B. Wright, Sawbridgeworth, Great Britain; Robert A. Zambias, Springfield, N.J.

[73] Assignee: Merck & Co., Inc., Rahway, N.J.

[21] Appl. No.: 230,825

[22] Filed: Aug. 12, 1988

[51] Int. Cl.$^5$ .................. A61K 31/34; A61K 31/44; C07D 307/79; C07D 405/12
[52] U.S. Cl. .................. 514/337; 514/469; 546/269; 549/462
[58] Field of Search .......... 549/462; 546/269; 514/337, 469

[56] References Cited

U.S. PATENT DOCUMENTS

| | | | |
|---|---|---|---|
| 2,388,579 | 11/1946 | Smith et al. | 549/462 |
| 3,812,079 | 5/1974 | Okutsu et al. | 524/111 |
| 4,386,072 | 5/1983 | Horrobin et al. | 424/722 |
| 4,537,903 | 8/1985 | Chang et al. | 549/462 |
| 4,558,067 | 12/1985 | Thompson et al. | 514/458 |
| 4,563,476 | 1/1986 | Chang et al. | 514/443 |
| 4,713,393 | 12/1987 | Chang et al. | 549/462 |
| 4,778,818 | 10/1988 | Chang et al. | 549/462 |
| 4,863,958 | 9/1989 | Belanger et al. | 549/471 |

FOREIGN PATENT DOCUMENTS 165810  12/1985  European Pat. Off. .

OTHER PUBLICATIONS

Zambias et al., J. Org. Chem. 53 (17), 4135–7 (Aug. 19, 1988).
Green, J. Chem. Soc., pp. 3362–3373 (1959).

*Primary Examiner*—Mary C. Lee
*Assistant Examiner*—Bernard I. Dentz
*Attorney, Agent, or Firm*—Curtis C. Panzer; Robert J. North; Joseph F. DiPrima

[57] ABSTRACT

Novel position-4 and/or position-6 substituted 5-hydroxy-2,3-dihydrobenzofuran and analogs of the following general structural formula (I) are disclosed:

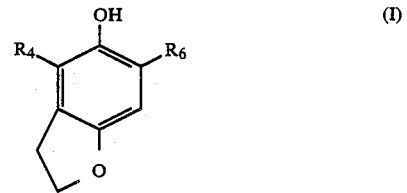

These compounds are found to be potent inhibitors of leukotriene biosynthesis.

10 Claims, No Drawings

6-SUBSTITUTED 5-HYDROXY-2,3-DIHYDROBENZOFURANS AS INHIBITORS OF LEUKOTRIENE BIOSYNTHESIS

BACKGROUND OF THE INVENTION

The present invention relates to novel four and/or six substituted 5-hydroxy-2,3-dihydrobenzofuran and analogs useful as inhibitors of leukotriene biosynthesis.

A number of 5-hydroxy2,3-dihydrobenzofurans have been known to have anti inflammatory activity. U.S. Pat. No. 4,558,067 issued Thompson, et al., on Dec. 10, 1985 discloses sulfur containing phenylthiomethyl-6-hydroxy-2,3-dihydrobenzo pyran and analogs thereof. U.S. Pat. No. 4,537,903 issued to Chang, et al., on Aug. 27, 1985, U.S. Pat. No. 4,686,235 issued to Chang, et al., on Aug. 11, 1987 and application 039,407 filed Apr. 17, 1987 now U.S. Pat. No. 4,778,818 disclose substituted cinnamyl-2,3-dihydrobenzofuran and analogs thereof. U.S. Pat. No. 4,563,476 issued to Chang, et al., on Jan. 7, 1986 discloses substituted-5-hydroxy-2,3-dihydrobenzofurans, wherein the substituent is linked to the benzofuran via a methylamine group. U.S. Pat. No. 4,713,393 issued to Chang, et al., on Dec. 15, 1987 discloses substituted phenyl-2,3-dihydrobenzofurans wherein phenyl substituents are linked to the benzofuran via a propyl moiety.

These patents, however, do not disclose the novel compound of the present invention nor do they disclose the ability of these compounds to inhibit leukotriene biosynthesis in vitro, by the polymorphonuclear leukocytes assay.

During the progression of inflammatory conditions, there is generally an appearance and/or presence of macrophages and lymphocytes, especially polymorphonuclear leukocytes. These cells are known to secrete various products in response to inflammatory stimuli. The arachidonic acid oxygenation products, in particular, have been identified as critical mediators of various inflammatory conditions. Inhibition of arachidonic acid oxidation by enzyme inhibition has been explored as effective therapy. For example, non-steroidal anti inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, *Science*, 220, 568 (1983); D. Baily et al, *Ann. Rpts Med. Chem.*, 17, 203 (1982)).

Accordingly, pharmacological agents which are capable of inhibiting the formation or the release of leukotrienes and thereby interfere with the function of macrophages, or polymorphonuclear leukocytes, may also be effective in the treatment of various inflammatory conditions, e.g., pain, fever, rheumatoid arthritis, osteoarthritis, bronchial inflammation, inflammatory bowel disease, asthma, allergic disorders, skin diseases, cardiovascular disorder, glaucoma, emphysema, acute respiratory distress syndrome, spondylitis, lupus, gout, and psoriasis.

The human polymorphonuclear leukocytes assay, has been found to be a useful indicator of the ability of compounds to inhibit leukotriene biosynthesis. Known inhibitors of leukotriene biosynthesis agents such as Phenidone and Nordihydroguaiaretic acid, for example, are active in this assay (C. J. Blackwell and R. J. Flower, Prostaglandins, 16, 417 (1978); J. Chang, M. D. Skowronek, M. L. Cherney and A. J. Lewis, Inflammation, 8, 143 (1984)).

DETAILED DESCRIPTION OF THE INVENTION

This invention relates to novel compounds of formula (I)

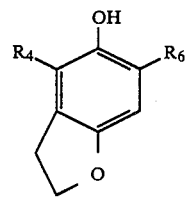

wherein:

$R_4$ is
(a) hydrogen;
(b) $C_{2-6}$alkenyl;
(c) $C_{1-6}$alkyl;
(d) substituted $C_{1-6}$alkyl wherein the substituent is:
 (1) phenylthio;
 (2) pyridyl $C_{1-6}$alkylthio;
 (3) hydroxyl;
 (4) phenoxy;
 (5) nitrile; or
 (6) phenamino;
(e) halo; or
(f) substituted $C_{1-6}$alkoxy wherein the substituent is
 (1) phenylthio;
 (2) pyridyl $C_{1-6}$alkylthio;
 (3) hydroxyl; or
 (4) pyridylthio;

$R_6$ is
(a) hydrogen;
(b) $C_{2-6}$alkenyl;
(c) $C_{1-6}$alkyl;
(d) substituted $C_{1-6}$alkyl wherein the substituent is:
 (1) phenylthio;
 (2) pyridyl $C_1-C_6$alkylthio;
 (3) hydroxyl;
 (4) cyano;
 (5) $C_{1-6}$carboxyl;
 (6) phenoxy;
 (7) phenylamino;
 (8) hydroxy $C_{1-6}$phenoxy;
 (9) $C_{1-6}$alkylphenoxy; or
 (10) halophenoxy;
(e) phenylthio;
(f) phenyl $C_{1-6}$alkylthio;
(g) pyridylthio;
(h) phenoxy;
(i) $C_{1-6}$alkoxy;
(j) substituted $C_{1-6}$alkoxy wherein the substituent is:
 (1) methoxy;
 (2) phenyl;
 (3) phenoxy;
 (4) carboxy $C_{1-6}$alkyl phenoxy, or their $C_1-C_6$ alkyl esters
 (5) carboxyphenoxy, or their $C_1-C_6$ alkyl esters;

(k) benzyl;
provided that when $R_4$ is hydrogen or $C_{1-6}$ alkyl, $R_6$ is other than hydrogen; or pharmaceutically acceptable salts thereof.

A first embodiment of the instant invention is the compounds of the formula (I) wherein $R_4$ is hydrogen.

A class of the first embodiment is the compounds of formula (I) wherein:
$R_6$ is
 (a) $C_{3-4}$alkyl;
 (b) $C_{3-4}$alkyl;
 (c) substituted $C_{3-4}$alkyl wherein the substituent is:
  (1) phenylthio;
  (2) pyridylmethylthio;
  (3) hydroxyl;
  (4) cyano;
  (5) $C_{2-3}$carboxyl;
  (6) phenoxy;
  (7) phenylamino;
  (8) hydroxy $C_{1-6}$alkylphenoxy;
  (9) $C_{2-4}$alkyl phenoxy; or
  (10) halophenoxy;
 (d) phenylthio;
 (e) phenyl $C_{1-6}$alkylthio;
 (f) pyridylthio;
 (g) phenoxy;
 (h) $C_{2-4}$alkoxy; or
 (i) substituted $C_{2-4}$alkoxy wherein the substituent is:
  (1) methoxy;
  (2) phenyl;
  (3) phenoxy;
  (4) carboxy $C_{1-6}$alkylphenoxy, or their $C_2-C_4$ alkyl esters; or
  (5) carboxyphenoxy, or their $C_{1-6}$alkyl esters; or
 (j) benzyl.

A subclass of the first embodiment is compounds of formula (I) wherein:
$R_6$ is
 (a) $C_{3-4}$alkenyl
 (b) $C_{3-4}$alkyl;
 (c) substituted $C_{3-4}$alkyl wherein the substituent is:
  (1) phenylthio;
  (2) pyridylmethylthio;
  (3) hydroxy $C_{2-4}$alkylphenoxy;
  (4) $C_{2-4}$alkylphenoxy;
  (5) halophenoxy; or
  (6) phenoxyphenamino;
 (d) phenyl $C_{1-6}$alkylthio;
 (e) $C_{2-4}$alkoxy;
 (f) substituted $C_{2-4}$alkoxy wherein the substituent is:
  (1) phenyl;
  (2) phenoxy; or
  (3) carboxy $C_{1-6}$alkylphenoxy; or their $C_2-C_4$alkyl esters;
 (g) phenylthio; or
 (h) benzyl.

A first group of species of the first embodiment are the following compounds:
 (a) 2,3-dihydro-6-(propen-3-yl)-5-benzofuranol;
 (b) 2,3-dihydro-6-propyl-5-benzofuranol;
 (c) 2,3-dihydro-6-(3-(3-thiomethylpyridyl)propyl)-5-benzofuranol;
 (d) N-Phenyl-3-(2,3-dihydro-5-benzofuranol-6-yl)propyl amine;
 (e) 2,3-dihydro-6-(3-(3-(2-hydroxyethyl)phenoxy)-propyl)-5-benzofuranol;
 (f) 2,3-dihydro-6-(phenylmethyl)-5-benzofuranol;
 (g) 2,3-dihydro-6-phenylthio-5-benzofuranol;
 (h) 2,3-dihydro-6-phenylmethylthio-5-benzofuranol;
 (i) 2,3-dihydro-6-butyloxy-5-benzofuranol;
 (j) 2,3-dihydro-6-(2-phenylethoxy)-5-benzofuranol;
 (k) 2,3-dihydro-6-(3-phenoxypropoxy)-5-benzofuranol; or
 (l) 2,3-dihydro-6-(1-methylethyl)-5-benzofuranol;
or pharmaceutically acceptable salts thereof.

A second group of species of the first embodiment are the following compounds:
 (a) 2,3-dihydro-6-(3-(phenylthio)propyl)-5-benzofuranol;
 (b) 2,3-dihydro-6-(3-phenoxypropyl)-5-benzofuranol;
 (c) 2,3-dihydro-6-(3-(4-(2-hydroxyethyl)phenoxy)-propyl)-5-benzofuranol;
 (d) 2,3-dihydro-6-(3-(3-(2-hydroxyethyl)phenoxy)-propyl)-5-benzofuranol;
 (e) 2,3-dihydro-6-(3-(4-propylphenoxy)propyl)-5-benzofuranol;
 (f) 2,3-dihydro-6-(2-phenylethyl)thio-5-benzofuranol
 (g) 2,3-dihydro-6-(3-phenylpropyl)thio-5-benzofuranol;
 (h) 2,3-dihydro-6-(3-(4-fluorophenoxy)propyl)-5-benzofuranol;
 (i) 2,3-dihydro-6-(3-(4-chlorophenoxy)propyl)-5-benzofuranol;
 (j) 2,3-dihydro-6-(3-phenylpropoxy)-5-benzofuranol;
 (k) 3-(3-((2,3-dihydro-5-hydroxy-6-benzofuranyl)oxy)propoxy)benzoic acid methyl ester;
 (l) 4-(3-((2,3-dihydro-5-hydroxy-6-benzofuranyl)oxy)propoxy)benzoic acid methyl ester; or
 (m) 4-(3-((2,3-dihydro-5-hydroxy-6-benzofuranyl)oxy)propoxy)benzeneacetic acid methyl ester;
or pharmaceutically acceptable salts thereof.

A second embodiment of the instant invention is the compounds of formula (I) wherein:
$R_4$ is
 (a) $C_{2-6}$alkenyl;
 (b) $C_{2-6}$alkyl;
 (c) substituted $C_{1-6}$alkyl wherein the substituent is:
  (1) phenylthio;
  (2) pyridyl $C_{1-6}$alkylthio;
  (3) hydroxyl;
  (4) phenoxy;
  (5) nitrilo; or
  (6) phenamino;
 (d) halo; or
 (e) substituted $C_{1-6}$alkoxy wherein the substituent is:
  (1) phenylthio;
  (2) pyridyl $C_{1-6}$alkylthio;
  (3) hydroxyl; or
  (4) pyridylthio; and
$R_6$ is hydrogen;
or pharmaceutically acceptable salts thereof.

A class of the second embodiment is the compounds of formula (I) wherein:
$R_4$ is
 (a) halo;
 (b) t-butyl;
 (c) phenoxypropyl; or
 (d) phenylthiopropyl.

A subclass of the second embodiment is compounds of formula (I) wherein:
$R_4$ is
 (a) phenoxypropyl; or
 (b) phenylthiopropyl.

Species of the second embodiment are the following compounds:

(a) 2,3-dihydro-4-(3-(phenylthio)propyl)-5-benzofuranol; or
(b) 2,3-dihydro-4-(3-phenoxypropyl)-5-benzofuranol;
or pharmaceutically acceptable salts thereof.

A third embodiment is the compounds of the formula (I) wherein:
$R_4$ is
(a) halo;
(b) methyl;
(c) t-butyl;
(d) phenoxypropyl; or
(e) phenylthiopropyl; and
$R_6$ is
(a) $C_{3-4}$alkenyl;
(b) $C_{3-4}$alkyl;
(c) substituted $C_{3-4}$alkyl wherein the substituent is:
  (1) phenylthio;
  (2) pyridylmethylthio
  (3) hydroxyl;
  (4) cyano;
  (5) $C_{2-3}$carboxyl;
  (6) phenoxy;
  (7) phenylamino;
  (8) hydroxy $C_{1-6}$phenoxy;
  (9) $C_{2-4}$alkylphenoxy; or
  (10) chlorophenoxy;
(d) phenylthio;
(e) phenyl $C_{2-4}$alkylthio;
(f) pyridylthio;
(g) phenoxy;
(h) $C_{2-4}$alkoxy; or
(i) substituted $C_{2-4}$alkoxy wherein the substituent is:
  (1) methoxy;
  (2) phenyl;
  (3) phenoxy;
  (4) carboxy $C_{1-6}$alkylphenoxy; or their $C_1$-$C_6$ alkyl esters; or
  (5) carboxy, phenoxyl; or their $C_1$-$C_6$ alkyl esters;
or pharmaceutically acceptable salts thereof.

A subclass of the second embodiment is compounds of formula (I) wherein:
$R_4$ is
(a) halo;
(b) methyl; or
(c) t-butyl; and
$R_6$ is
(a) $C_{3-4}$alkenyl;
(b) $C_{3-4}$alkyl;
(c) phenylthio $C_{3-4}$alkyl;

A first group of species of the third embodiment are the following compounds:
(a) 2,3-dihydro-4-methyl-6-(propen-3-yl)-5-benzofuranol;
(b) 2,3-dihydro-4-methyl-6-propyl-5-benzofuranol; or
(c) 2,3-dihydro-4-t-butyl-6-propyl-5-benzofuranol;
or pharmaceutically acceptable salts thereof.

A second group of species of the third embodiment are the following compounds:
(a) 2,3-dihydro-4-methyl-6-(3-(phenylthio)propyl
(b) 2,3-dihydro-4-bromo-6-propyl-5-benzofuranol;
or pharmaceutically acceptable salts thereof.

The compounds of the present invention are conveniently prepared using the procedures described generally below and more explicitly in the Examples section thereafter.

The terms $R'_4$, $R'_5$ and $R'_6$ in the accompanying preparatory schemes I to IV indicate the point of further modification to the position-4, position-5 or position-6 substituent respectively. The terms $R_4$ and $R_6$ are as defined in formula I.

SCHEME I

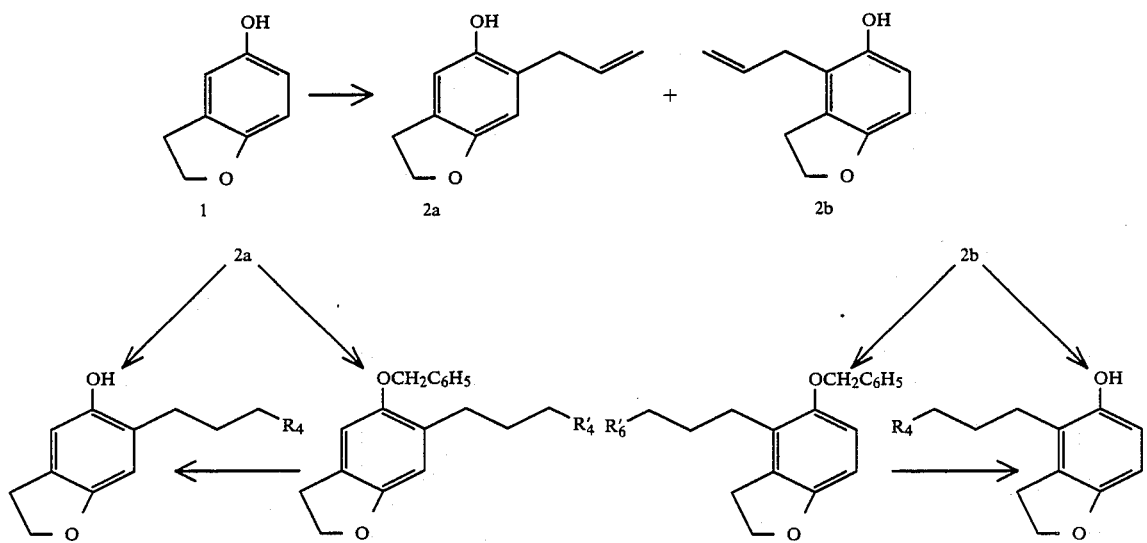

Scheme I depicts compounds that may be prepared en route to position-4 and position-6 substituted and unsubstituted alkyls, alkenyls and derivatives thereof within the first and second embodiment of the invention. Alkylation of 1 with allyl bromide followed by Claisen rearrangement affords 2a and 2b.

The 6-allyl compound is catalytically hydrogenated to the unsubstituted alkyl. Alternatively the allyl is functionalized under free radical conditions with a mercaptan such as thiophenol to yield the corresponding thioalkyl. (Stacey, F. W.; Harris, J. F.; Org. Reactions 1963, 13, 155; Fisher, A.; King, M. J.; Robinson, F. P. Can. J. Chem. 1978, 56, 3068; Fisher, M. J.; King, M. J.; Robinson, F. P. Can. J. Chem. 1978, 56, 3059.) Hydroboration of the 6 allyl with a suitable borane such as borane methyl sulfide in an ether solvent followed by oxidation of the intermediate organoborane results in the 6 hydroxyalkyl. The monosodium salt of the alcohol is then quenched with a phenyl alkylhalide to yield the position-5 phenylalkoxy which is then directly converted to the primary tosylate as exemplified by 2,3-dihydro-6-(3-hydroxypropyl)-5-benzyloxy benzofuran 8a.

Displacement of the tosylate 8a with a variety of nucleophiles as sodium cyanide, lithium anilide or sodium phenoxide in an appropriate solvent such as ethanol, dimethyl formamide, DMSO or THF followed by deprotection by catalytic hydrogenation provides access to an additional series of 6-substituted compounds.

In an identical fashion to that described above for the 6-allyl compound 2a, the 4-allyl Compound, 2b, provides synthetic access to a like series of 4-substituted 2,3-dihydro-5-benzofuranols.

ing 7-position product. Bromination of 1 afforded 16 (previously described). Protection of 16 as the methoxymethyl ether gave 17 which was readily converted to the 6-lithioderivative by treatment with either n-butyllithium or tert-butyllithium. Selander, H.; Nilsson, J. L. G. Acta Chem. Scand. 1972, 26, 2433; Svensson, K. G. Selander, H.; Karlsson, M.; Nilsson J. L. G. Tetrahedron 1973, 29, 1115; Van Heerden, F. R.; Van Zyl, J. J.; Rall, G. J. H.; Brandt E. V.; Roux, D. G. Tet. Lett. 1978, 661., Quenching the lithium reagent with a series of disulfides afforded, after deprotection, 6-phenyl sulfides, phenyl $C_{1-6}$alkyl sulfides and pyridyl- sulfides exemplified by compounds 18a to 18d. Alternatively the lithio anion of 17 is alkylated with alkyl and aryl iodides and deprotected at position-5 to give 6-phenoxyalkyl and halophenoxy alkyls exemplified by 11a, 19a and 19b. Ullmann coupling of 17 with a phenol in the presence of cupric oxide and pyridine affords, after deprotection at position 5, such products as the 6-phenoxy. (See Djura, P.; Sargent, M. V.; Vogel, P. J. Chem. Soc. Perkin I 1976, 147.)

SCHEME II

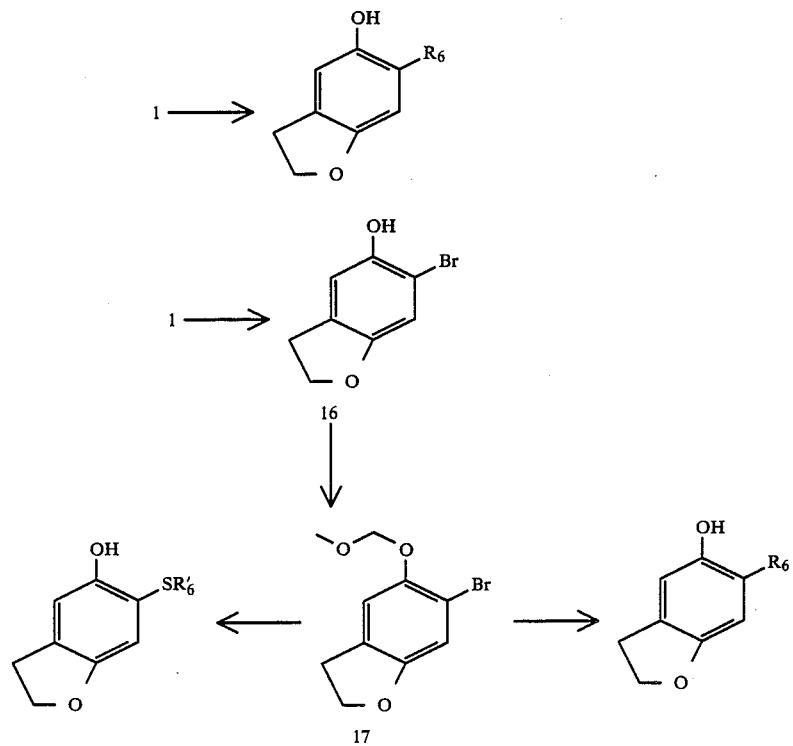

Scheme II depicts compounds produced en route to an additional series of 6-substituted analogs. Direct electrophilic alkylation of 1 with a tert-alkyl alcohol in benzene using sulfuric acid as a catalyst results a mixture of the position-6 tertiary alkyl and the corresponding

SCHEME III

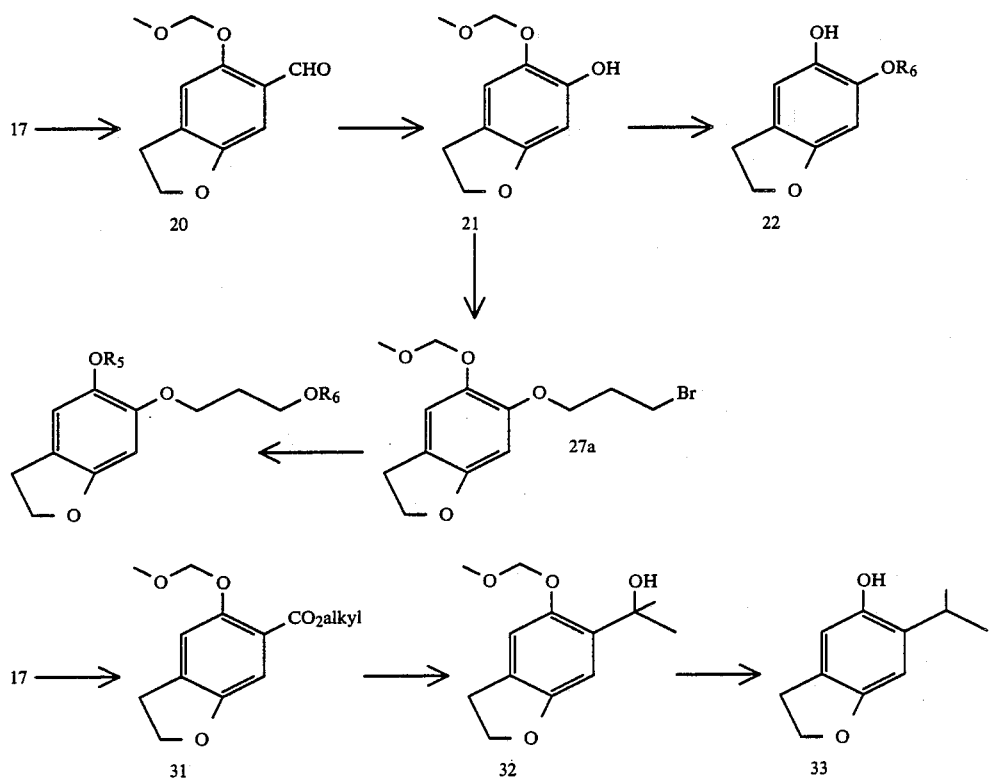

Synthetic access to 6-substituted alkyl ether analogs of 1 is depicted in Scheme III, by the reaction sequence beginning with 17.

Acylation of the lithio anion of 17 gives the aldehyde exemplified by 20, which is oxidized with such compounds as p-nitroperbenzoic acid or m-chloroperbenzoic acid to afford the monoprotected catechol as exemplified by 21. (See Rastetter, W. H.; Richard, T. J.; Lewis, M. D. J. Org. Chem. 1978, 43, 3163. The monoprotected catechol is alkylated with the requisite alkyl halide, which after deprotection gives alkyl and substituted alkyl ethers such as 22a to 22d. Alkylation of the sodium alkoxide of the monoprotected catechol in dimethylformamide with 1,3-dibromopropane affords 27a. In an analogous fashion alkylation of the sodium salt of the three isomeric alkyl hydroxybenzoates and alkyl 4-hydroxyphenylalkylate with 27a results in the corresponding alkyl phenyl ether exemplified by 23b, 25, 27b, and 29. The position-5 protecting group of such compounds is removed with dilute methanolic HCl to give the deprotected methyl esters (R'$_5$=H such as 24, 26, 28, and 30. Alternatively the 6 postion esters (e.g. 23b, 25, and 29) is saponified and the crude carboxylic acids deprotected in dilute aqueous HCl containing tetrahydrofuran as a cosolvent, to give the corresponding alkyl phenyl carboxylic acid derivative.

Introduction of a branched chain at the 6-position is also achieved. Once again this is illustrated by the reaction sequence beginning with the bromide 17. Addition of the lithio anion of 17 to alkyl chloroformate results in alkyl ester products as exemplified by 31 which is treated with a small excess of alkyllithium to afford a 6-dialkyl carbinol exemplified 32. Lithium ammonia reduction of the carbinol proceeded, after deprotection, to give the dialkyl methyl, such as 33. (Small, G. H.; Minnella A. E.; Hall, S. S. J. Org. Chem. 1975, 40, 3151.)

SCHEME IV

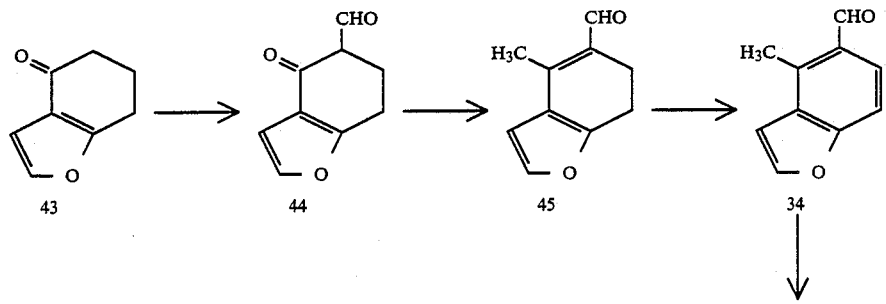

SCHEME IV -continued

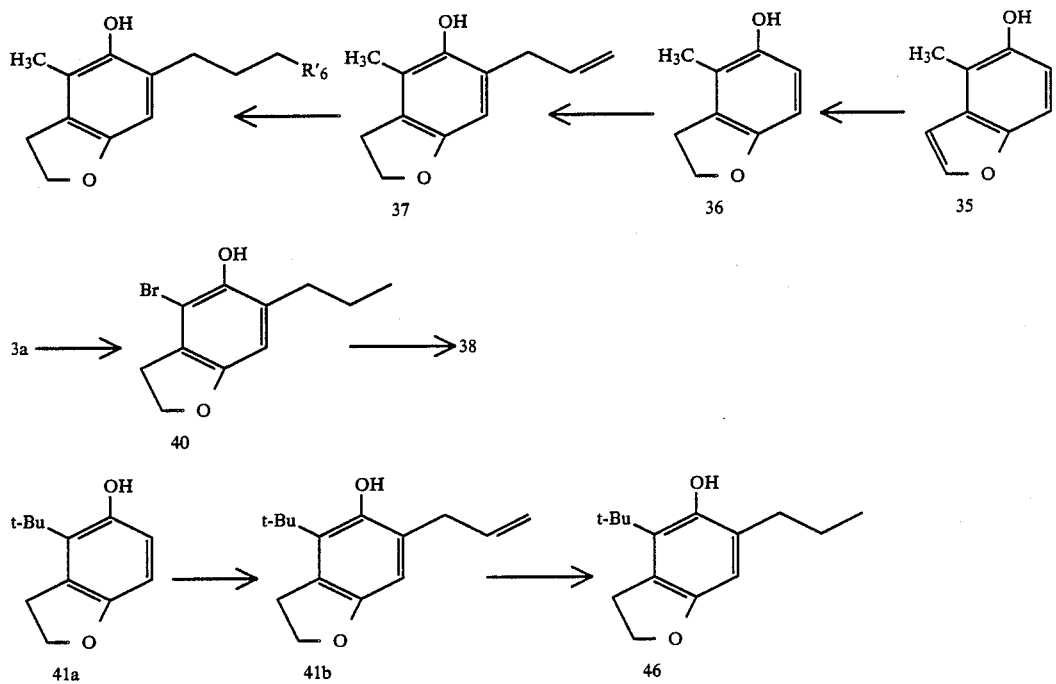

Preparation of 4,6-disubstituted dihydro-5-benzofuranols within the third embodiment of the invention is shown in Scheme IV. The reaction scheme is exemplified beginning with the previously described benzofuranone 43. Formylation of 43 by known procedures such as with sodium hydride and alkyl formate in toluene gives 44. (Remers, W. A.; Jones, G. S., J. Heterocycl. Chem. 1975, 12, 421) ((a) Yamakawa, K.; Satch, T.; Chem. Pharm. Bull. 1977, 25, 2535; (b) Most; L.; Shenone, P.; Menozzi, G; Romussi, G., Eur. J. Med. Chem. Chim. Ther. 1983, 18, 113). The 6-formyl derivative 44 can then be converted to the enol silyl ether and added directly to a −78° C. solution of methyllithium. (Tius, M. A.; Ali, S. J. Org. Chem. 1982, 47, 3163.) Mild acidic hydrolysis of 44 results in the 4-methyl compound 45. Oxidation with DDQ (2,3-dichloro 5,6-dicyano-1,4-benzoquinone) afforded 34 which is converted to the phenol 35 by Baeyer Villager reaction followed by saponification. Hydrogenation over 10% palladium on carbon gives the known dihydrobenzofuranol 36 which is alkylated with allyl bromide and rearranged as described for 1 to the 6-allyl analog 37. (Green, J.; McHale, D.; Marcinkeiwicz, S.; Mamalis, P.; Watt, P. R. J. Chem. Soc. 1959., 3362). Analog 37 can then be hydrogenated to the 6-alkyl ($R_6' = H$) or alkylated under free radical conditions with a mercaptan such as a thiophenol ($R_6' = SC_6H_5$). Sterically encumbered analogs as exemplified by 46 are prepared from the phenol 41a as described in the Examples Section by alkylation with allyl bromide and Claisen rearrangement to give 41b. Simple hydrogenation then affords 46.

This invention also relates to a method of treating leukotriene mediated diseases as described above in patients in need of such treatment. Generally, an effective non toxic amount of a compound of formula (I) or a pharmaceutical composition thereof, particularly an especially preferred compound, is administered to the patient as the active constituent.

To demonstrate the utility of the present invention, representative novel compounds of formula I were evaluated for their ability to inhibit production of $LTB_4$ in isolated human polymorphonuclear leucocytes (PMN). Other compounds known to inhibit leulotriene biosynthesis have been shown to have activity in this assay.

A. Preparation of Human PMN

Human blood is obtained by antecubital venepuncture from consenting volunteers who denied having taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation and centrifugation through Ficoll Hypaque (specific gravity 1.077), essentially as described by Boyum. (Boyum, A., Scand. J. Clin. Lab. Invest 1968, 21 (Supp 97), 77). Contaminating erythrocytes are removed by lysis following exposure to ammonium chloride (0.16M) in Tris buffer (pH 7.65), and the PMNs resuspended at $5 \times 10^5$ cells/mL in HEPES (15 mM) buffered Hanks balanced salt solution containing $Ca^{2+}$ (1.4 mM) and $Mg^{2+}$ (0.7 mM), pH 7.4. Viability is assessed by Trypan blue exclusion and is typically greater than 98%.

B. Generation and Radiommumoassay of $LTB_4$

PMNs 0.5 mL; $2.5 \times 10^5$ cells) are placed in plastic tubes and incubated (37° C., 2 min) with test compounds at the desired concentration or vehicle control (DMSO, final concentration 0.2%). The synthesis of leukotriene $B_4$ ($LTB_4$) is initiated by the addition of calcium ionophore A23187 (final concentration 10 μM) or vehicle on control samples and allowed to proceed for 5 minutes at 37° C. The reactions are then terminated by the addition of cold methanol (0.25 mL) and samples of the entire PMN reaction mixture are removed for radiommunoassay of $LTB_4$.

Samples (50 μl) of authentic $LTB_4$ of known concentration in radiommunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes.

Thereafter [3H]$LTB_4$ (10 nCu in 100 μl RIA buffer) and $LTB_4$ antiserum (100 μL of a 1:3000 dilution in RIA buffer) are added and the tubes vortexed. Reactants are allowed to equilibrate by incubation overnight at 4° C. To separate antibody bound from free $LTB_4$, aliquots (50 μL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatents containing antibody-bound $LTB_4$ are decanted into vials and Aquasol 2 (4 mL) is added. Radioactivity is quantified by liquid scintillation spectrometry. Preliminary studies established that the amount of methanol carried into the radioimmunoassay did not influence the results. The specificity of the antiserium and the sensitivity of the procedure have been described in detail elsewhere. (Rokach, J.; Hayes, E. C.; Girard, Y.; Lombardo. D. L.; Maycock, A. L.; Rosenthal, A. S.; Young, R. N.; Zamboni, R.; Zweerink, H. J. Prostaglandins Leukotrienes and Medicine 1984, 13, 21). The amount of $LTB_4$ produced in test and control (approx. 20 ng/$10^6$ cells) samples are then calculated. Inhibitory dose response curves are constructed using a four-parameter algorithm and from these the $IC_{50}$ values are determined.

Standard compounds phenidone and nordihydroguaiacetic acid, when evaluated by the above described in vitro test, demonstrate $IC_{50}$ values for $LTB_4$ inhibition of 9250 and 86 nanomolar respectively. As indicted below representative compounds within the scope of the present invention have been found to possess in vitro activities superior to those of these standard compounds.

| Human Polymorphonuclear Leucocyte Activity of Specific Compounds | | |
| --- | --- | --- |
| $R_4$ | $R_6$ | $IC_{50}$ (nM) |
| H | $(CH_2)_3SC_6H_5$ | 19 |
| H | $(CH_2)_3OC_6H_5$ | 57 |
| H | $(CH_2)_3OC_6H_4$-4-$(CH_2)_2OH$ | 41 |
| H | $(CH_2)_3OC_6H_4$-3-$(CH_2)_2OH$ | 77 |
| H | $(CH_2)_3OC_6H_4$-4-$(CH_2)_2CH_3$ | 9 |
| H | $S(CH_2)_2C_6H_5$ | 66 |
| H | $S(CH_2)_3C_6H_5$ | 28 |
| H | $(CH_2)_3OC_6H_4$-4-F | 28 |
| H | $(CH_2)_3OC_6H_4$-4-Cl | 55 |
| H | $O(CH_2)_3C_6H_5$ | 51 |
| H | $O(CH_2)_3OC_6H_5$-2-$CO_2CH_3$ | 65 |
| H | $O(CH_2)_3OC_6H_5$-3-$CO_2CH_3$ | 56 |
| H | $O(CH_2)_3OC_6H_5$-4-$CO_2CH_3$ | 71 |
| H | $O(CH_2)_3OC_6H_5$-4-$CH_2CO_2CH_3$ | 72 |
| $CH_3$ | $(CH_2)_3SC_6H_5$ | 19 |
| Br | $CH_2CH_3CH_3$ | 49 |

For the treatment of inflammation, arthritis conditions, psoriasis, asthma, or other diseases mediated by leukotrienes, a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelation or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydrides, for example, sorbitan mono-oleate, and condensation products of the said partial esters with enthylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sevacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above indicated condition (10 mg to 7 gms per patient per day). For example, leukotriene biosynthesis is effectively treated by the administration from about 0.5 to 50 mg of the compound per kilogram of body weight per day (25 mg to 5 gms per patient per day).

The amount of active ingredient that may be combined with the carrier materials to produce a single dosage will vary depending upon the host treated and the particular mode of administration. Dosage unit forms will generally contain from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the preparation of the compounds of the formula (I) and as such are not to be considered as limiting the invention set forth in the claims appended hereto.

EXAMPLE 1

2,3-dihydro-5-hydroxybenzofuran (1)

Preparation of 1 is well known in the art. C. Selander, H.: Nilsson, J. L. G. Acta Chem. Scand. 1972, 26, 2433; Pearlman, W. M. Tet. Lett. 1967, 17,

EXAMPLE 2

2,3-dihydro-6-(propen-3-yl)-5-benzofuranol (2a) and 2,3-dihydro-4-(propen-3-yl)-5-benzofuranol. (2b)

Step A. To a mechanically stirred mixture of 1 (35.00 g, 257 mmol) and anhydrous potassium carbonate (175.00 g, 1.27 mol) in acetone (750 mL) was added allyl bromide (63 mL, 88.0 g, 728 mmol) and the mixture heated to reflux for 16 hours. The reaction mixture was allowed to cool, and the salts removed by filtration. The filtrate was concentrated and distilled to give the allyl ether bp 102° C. at 0.9 mmHg.

Step B. The allyl ether from Step A (3.50 g, 19.8 mmol) was heated to 200° C. under nitrogen until starting material was consumed by TLC (20% ethyl acetate in hexane as eluant, 2 hours). After cooling the residue was purified by flash chromatography using 10% ethyl acetate in hexane as eluant to afford in order of elution 2b and 2a. 2a: mp, 80°-82° C.

| Micro analysis for 2a: | C | H |
| --- | --- | --- |
| Calc'd; | 74.97 | 6.84 |
| Found: | 75.08 | 6.95 |
| Micro analysis for 2b: | C | H |
| Calc'd: | 74.97 | 6.84 |
| Found: | 75.08 | 6.91 |

EXAMPLE 3

2,3-dihydro-6-propyl-5-benzofuranol (3)

A solution of 2a (10.00 g, 56.8 mmol) in absolute ethanol (100 mL) was hydrogenated over 10% palladium on carbon catalyst (0.500 g) at 3 atmospheres pressure. After the requisite amount of hydrogen had been taken up (30 minutes) the catalyst was removed by filtration through celite and the filtrate concentrated. Preparative HPLC using 10% ethyl acetate in hexane as eluant gave 3. 3: mp 73°-74° C.

| Micro analysis for 3: | C | H |
| --- | --- | --- |
| Calc'd: | 74.14 | 7.92 |
| Found: | 73.84 | 7.71 |

EXAMPLE 4

2,3-dihydro-6-(3-(phenylthio)propyl)-5-benzofuranol (4a)

To a solution of 2a (0.600 g, 3.40 mmol) in thiophenol (1.5 mL) was added AIBN (azobisisobutyronitrile) (0.150 g) and the mixture heated at 90° C. for 8 hours. The mixture was cooled and the excess thiophenol removed under reduced pressure. Flash chromatography using 20% ethyl acetate in hexane as eluant gave in order of elution 2a and 4a.

In a manner analogous to that described for 4a, 2b (1.00 g, 5.67 mmol) was treated with thiophenol (3 mL) and AIBN (0.260 g) to give 4b and recovered 2b. 4b: mp 87°–88° C.

| Micro analysis for 4a: | C | H | S |
|---|---|---|---|
| Calc'd: | 71.30 | 6.33 | 11.20 |
| Found: | 71.43 | 6.43 | 11.08 |
| Micro analysis for 4b: | C | H | S |
| Calc'd: | 71.30 | 6.33 | 11.20 |
| Found: | 71.31 | 6.46 | 11.14 |

EXAMPLE 5

2,3-dihydro-6-(3-(3-pyridylthiomethyl)propyl)-5-benzofuranol (5)

In a manner analogous to that described for 4a, 2a (0.375 g, 2.13 mmol) was treated with 3-thiomethylpyridine (1.05 g, 8.38 mmol) and AIBN (0.088 g) to afford 5. 5: mp 130°–131° C.

| Micro analysis for 5: | C | H | N | S |
|---|---|---|---|---|
| Calc'd: | 67.74 | 6.35 | 4.65 | 10.64 |
| Found: | 68.06 | 6.24 | 4.54 | 10.79 |

EXAMPLE 6

2,3-dihydro-6-(3-hydroxypropyl)-5-benzofuranol (6)

To a 5° C solution of 2a (15.00 g, 88.0 mmol) in ether (125 mL) was added neat borane methyl sulfide (5.4 mL, 4.33 g, 56.9 mmol) and the mixture allowed to stir at room temperature for 1 hour. Absolute ethanol (100 mL) was added followed by 2.5 N NaOH (155 mL). The solution was cooled to 5° C. and 30% hydrogen peroxide (14.1 mL) was added dropwise. The resulting mixture which had warmed to 25°–30° C. during the peroxide addition was allowed to stir for 30 minutes. The reaction was then worked up by diluting with water (300 mL) and extracting with ether (3×200 mL). The combined ether extracts were washed sequentially with water and 20% NaCl, dried (MgSO$_4$), and concentrated. Recrystallization from chloroform gave 6. Chromatography of the mother liquors using 40% ethyl acetate in hexane as eluant afforded additional 6. 6: mp 103°–104° C.

| Micro analysis for 6: | C | H |
|---|---|---|
| Calc'd: | 68.04 | 7.26 |
| Found: | 67.74 | 7.42 |

EXAMPLE 7

2,3-dihydro-6-(3-hydroxypropyl)-5-benzyloxy benzofuran (7)

Sodium hydride (60% dispersion in mineral oil, 0.678 g, 16.95 mmol) was washed with petroleum ether then suspended in dry tetrahydrofuran (15 mL) and cooled in an icebath. A solution of 6 (3.00 g, 15.4 mmol) in dry tetrahydrofuran (16 mL) was added dropwise to the sodium hydride suspension. When the hydrogen evolution had ceased, benzyl bromide (3.03 g, 17.7 mmol) was added dropwise and the mixture allowed to stir at room temperature overnight. The reaction was diluted with hexane (20 mL), filtered, and the filtrate concentrated. The residue was taken up in ether (50 mL), washed with 2N HCl and brine, dried (MgSO$_4$) and concentrated to give 7.

EXAMPLE 8

2,3-dihydro-6-(3-hydroxypropyl)-5-benzyloxybenzofuran tosylate (8a)

To a 0° C. solution of 7 (1.16 g, 4.07 mmol) in dry pyridine (3 mL) was added p-toluenesulfonyl chloride (0.707 g, 2.72 mmol) and the mixture allowed to warm to room temperature and stir for 1 hour. The reaction mixture was poured into ice water (25 mL) and acidified with 2N HCl. The resulting precipitate was collected by filtration, washed with water (2×5 ML), and vacuum dried to give 8a. 2,3-Dihydro-4-(3-hydroxypropyl)-5-benzyloxybenzofuran tosylate (8b) can be produced in similar fashion

EXAMPLE 9

4-(2,3-dihydro-5-benzyloxybenzofuran-6-yl)butyronitrile (9a); and 4-(2,3-dihydro-5-benzyloxybenzofuran-6-yl)butanoic acid (9b)

A mixture of 8a (1.28 g, 2.91 mmol) and sodium cyanide (0.300 g, 6.12 mmol) in 95% ethanol (5 mL) and dimethylformamide (1 mL) was heated to reflux until the starting tosylate was no longer present by TLC (30% ethyl acetate in hexane as eluant). The reaction was worked up by pouring into water and extracting with ethyl acetate. The organic extract was washed with water and 20% NaCl, dried (Na$_2$SO$_4$) and concentrated. The residue was purified by flash chromatography using 25% ethyl acetate in hexane as eluant to give 9a as an oil.

To a solution of potassium hydroxide (85%, 0.724 g, 10.00 mmol) in water (2 mL) and ethanol (2 mL) was added 9a (0.290 g, 1.01 mmol) and the mixture heated to reflux for 18 hours. The reaction mixture was cooled, acidified with 2N HCl, and extracted with ether. The extract was dried (MgSO$_4$) and concentrated to a solid. Recrystallization from hexane/ether gave 9b.

EXAMPLE 10

4-(2,3-dihydro-5-benzofuranol-6-yl)butanoic acid (10)

To a solution of the acid 9b (0.100 g, 0.32 mmol) in absolute ethanol (1 mL) was added 10% palladium on carbon (0.015 g) and the mixture hydrogenated at atmospheric pressure overnight. The catalyst was removed by filtration and the filtrate concentrated to give 10. 10: mp 121°–123° C.

| Micro analysis for 10: | C | H |
|---|---|---|
| Calc'd: | 63.32 | 6.43 |
| Found: | 63.53 | 6.37 |

EXAMPLE 11

2,3-dihydro-6-(3-phenoxypropyl)-5-benzofuranol (11a)

A solution of 8a (0.440 g, 1.01 mmol) in dry dimethylformamide (1 mL) was added to a solution of sodium phenoxide (0.140 g, 1.20 mmol) and the mixture heated to 80° C. for three hours. The reaction mixture was cooled, poured into water, and extracted with ether. The ether extracts were washed sequentially with water and 20% NaCl, dried (Na₂SO₄), and concentrated. Flash chromatography gave a purified benzyl ether (0.210 g, mp 81°-82° C.) which was directly deprotected as described above for 10 to give 11a. 2,3-Dihydro-4-(3-phenoxypropyl)-5-benzofuranol (11b) can be produced from 8b in similar fashion. 11a: mp 114–115° C.; 11b: mp 107°–108° C.

| Micro analysis for 11a: | C | H |
|---|---|---|
| Calc'd: | 75.55 | 6.71 |
| Found: | 75.56 | 6.51 |

EXAMPLE 12

N-Phenyl-3-(2,3-dihydro-5-benzyloxybenzofuran-6-yl)-propyl amine (12)

To a −78° solution of lithium anilide, prepared from aniline (0.217 g, 2.33 mmol) and n-butyllithium (1.6 M in hexane, 1.46 mL, 2.33 mmol), in tetrahydrofuran (2 mL) was added a solution of 8a (0.980 g, 2.23 mmol). Dimethyl sulfoxide (0.1 mL) was added and the mixture was allowed to stir at room temperature for 1 hour. The reaction mixture was poured into water and extracted with ether (2 X). The extracts were dried (MgSO₄) and concentrated to afford 12.

EXAMPLE 13

N Phenyl-3-(2,3-dihydro-5-benzofuranol-6-yl)propyl amine (13)

A solution of 12 (0.800 g, 2.22 mmol) in absolute ethanol (5 mL) containing acetic acid (1 mL) was hydrogenated over 10% palladium on carbon (0.040 g) at 3 atmospheres for 8 hours. The catalyst was removed by filtration and the filtrate diluted with water (10 mL) and ether (10 mL). The mixture was neutralized with solid NaHCO₃ and the layers separated. The aqueous layer was reextracted with ether (4×10 mL) and the combined ether extracts dried (MgSO₄) and concentrated. Flash chromatography using 25% ethyl acetate in hexane as eluant afforded 13. 13: mp 132°–133° C.

| Micro analysis for 13: | C | H | S |
|---|---|---|---|
| Calc'd: | 75.82 | 7.11 | 5.20 |
| Found: | 75.50 | 7.22 | 4.94 |

EXAMPLE 14

2,3-dihydro-6-(3-(4-(2-hydroxyethyl)phenoxy)propyl)-5-benzofuranol (14a)

To a solution of 4-hydroxyphenethyl- alcohol (0.249 g, 1.80 mmol) in dry tetrahydrofuran (3 mL) was added n-butyllithium (1.6 M in hexane, 1.13 mL, 1.85 mmol) and the mixture allowed to stir for ten minutes. The solvent was removed under reduced pressure and the residue resuspended in dimethylsulfoxide sulfoxide (3 mL) containing tetramethylethylenediamine (0.45 mL, 3 mmol). To the resulting solution was added 8a (0.657 g, 1.50 mmol) and the mixture stirred at room temperature for 16 hours. The mixture was poured into water (50 mL) and extracted with ether (3×50 mL). The combined extracts were dried (MgSO₄), concentrated, and purified by flash chromatography (40% ethyl acetate in hexane as eluant) to give a solid (0.500 g, mp 101°–102° C.). This material was hydrogenated as a solution in ethanol (10 mL) over 10% palladium on carbon (0.035 g). After filtration and concentration the crude hydrogenation product was recrystallized from ethyl acetate/hexane to give 14a. 14a: mp 116°–117° C.

2,3-Dihydro-6-(3-(3-(2-hydroxyethyl)-phenoxy)-propyl)-5-benzofuranol (14b); 2,3-dihydro-6-((3-(2-(2-hydroxyethyl)phenoxy)propyl)-5-benzofuranol (14c); and 2,3-dihydro 6-(3-(4-propylphenoxy)propyl)-5-benzofuranol (14d) can be produced by following the procedure as outlined for 14a followed by treatment with the appropriate lithium phenol salt and subsequent deprotection. 14b: mp 71°–72° C.; 14c: mp 131°–132° C; 14d: mp 101°–102° C.

EXAMPLE 15

2,3-dihydro-6-t-butyl-5-benzofuranol (15a)

To a solution of 1 (1.00 g, 7.35 mmol) and t-butanol (0.82 g, 11.00 mmol) in benzene (20 mL) was added concentrated H₂SO₄ (0.20 mL) and the mixture heated to 60° C. After 1 hour an additional portion of t-butanol (0.82 g, 11.00 mmol) and concentrated H₂SO₄ (0.2 mL) was added and heating continued for another 1.5 hours. At this point starting material had been consumed and two products were apparent by TLC (3:1 methylene chloride/hexane). The reaction mixture was diluted with ether (30 mL) and quenched with 5% NaHCO₃ (100 mL). The layers were separated and the aqueous phase back extracted with an additional portion of ether (25 mL). The combined organic layers were dried (Na₂SO₄), and concentrated. Purification by flash chromatography using 3:1 methylene chloride/hexane as eluant afforded in order of elution 15a and 2,3-dihydro-7-t-butyl-5-benzofuranol. 2,3-Dihydro-6-(phenylmethyl)-5-benzofuranol (15b) can be produced from Compound 1 in similar fashion. 15a: mp 146.5°–148° C.; 15b: mp 133°–135° C.

EXAMPLE 16

2,3-dihydro-6-bromo-5-benzofuranol (16)

A 3 liter 3-neck flask fitted with a mechanical stirrer was charged with 1 (100 g, 735 mmol) in methylene chloride (1500 mL) and a solution of bromine (122 g, 763 mmol) in dichloromethane (total volume 250 mL) was added dropwise over 1.5 hours. Upon completion of the addition the mixture was allowed to stir at room temperature then worked up in two batches as follows. Approximately half of the reaction mixture was poured into 5% NaHCO₃ (2000 mL) and the resulting mixture allowed to stir for 30 to 60 minutes. The layers were separated and the aqueous layer reextracted with methylene chloride (500 mL). The combined organic extracts were washed with 5% NaHSO₃ (500 mL), dried with MgSO₄, filtered and all the organic fractions combined. The product crystallized upon concentration and were therefore triturated in small batches to afford 16 as a tan solid.

EXAMPLE 17

2,3-dihydro-6-bromo-5-benzofuranol methoxymethyl ether (17)

A flame-dried 1000 mL 3-neck flask fitted with an internal thermometer, magnetic stirring, and a 250 mL dropping funnel was charged with sodium hydride (60% dispersion in mineral oil, 11.17 g, 279 mmol) and dimethylformamide (dried over molecular sieves, 200 mL). A solution of 16 (50.00 g, 233 mmol) in dimethylformamide (100 mL) was added dropwise such that the reaction temperature did not exceed 40° C (addition time was approximately 30 minutes). When hydrogen evolution had ceased, an ice bath was added and chloromethyl methylether (22.47 g, 297 mmol) was added dropwise at 25° C. Upon completion of the addition the reaction mixture was allowed to stir at room temperature for two hours then quenched by pouring into water (1000 mL). The mixture was extracted with ether (3×300 mL) and the combined organic extracts washed sequentially with water (2×500 mL) and 20% NaCl (300 mL), dried (Na$_2$SO$_4$), and concentrated. Distillation afforded 17 as a colorless liquid.

EXAMPLE 18

2,3-dihydro-6-phenylthio-5-benzofuranol (18a)

To a solution of 17 (3.00 g, 11.6 mmol) in dry tetrahydrofuran (50 mL) at −60° was added dropwise a solution of n-butyllithium (1.56 M in hexane, 8.25 mL, 13.0 mmol) and the mixture allowed to stir for 20 minutes. To the resulting white suspension was added dropwise a solution of diphenyl disulfide (4.00 g, 18.5 mmol) in tetrahydrofuran (20 mL) and the mixture allowed to stir for 20 minutes at −60° C. then warmed to room temperature over 40 minutes. The reaction mixture was poured into water (150 mL) and extracted with ether (3×100 mL). The combined extracts were dried (Na$_2$SO$_4$) and concentrated. The crude product (5.0 g) was purified by preparative HPLC using 10% ethyl acetate in hexane as eluant then directly deprotected in methanol (40 mL) containing concentrated HCl (0.25 mL) at 50° C. for 3 hours. Most of the methanol was removed in vacuo and the residue partitioned between ethyl acetate (75 mL) and water (25 mL). The organic extract was washed with an additional portion of water (25 mL), dried (Na$_2$SO$_4$), and concentrated. Flash chromatography using 10% ethyl acetate in hexane afforded 18a. 18a: mp 80°-81° C. Recrystallization from hexane gave an analytical sample. 2,3-Dihydro-6-phenylmethylthio-5-benzofuranol (18b); 2,3-dihydro 6 (2 phenylethyl)thio-5-benzofuranol (18c) and 2.3-dihydro-6-3-phenylpropyl)thio-5-benzofuranol (18d) can be produced from 17 in similar fashion. 18b: mp 50°-52° C.; 18c and 18d are oils.

| Micro analysis for 18a: | C | H | S |
|---|---|---|---|
| Calc'd: | 68.83 | 4.95 | 13.12 |
| Found: | 68.75 | 5.21 | 13.01 |
| Micro analysis for 18b: | C | H | S |
| Calc'd: | 69.74 | 5.46 | 12.41 |
| Found: | 70.19 | 5.63 | 12.18 |
| Micro analysis for 18c: | C | H | S |
| Calc'd: | 71.31 | 6.34 | 11.20 |
| Found: | 71.18 | 6.28 | 10.97 |

EXAMPLE 19

2,3-dihydro-6-(3-(4-fluorophenoxy)propyl)5-benzofuranol (19a)

In a manner analogous to that described above for 11a, 17 (6.78 g, 26.1 mmol) was converted to its lithium salt with t-butyllithium (1.7 M in pentane, 33.3 mL, 56.6 mmol) and alkylated with 4-fluorophenoxypropyl iodide (7.33 g, 26.1 mmol). (The 4-fluorophenoxypropyl iodide and 4-chlorophenoxypropyl iodide were prepared from the substituted phenols by treatment with 1,3-dibromopropane as described for 27a, followed by displacement of the bromide with sodium iodide in acetone.) The crude alkylation product was deprotected to give 19a. 2,3-Dihydro-6-(3-(4-chlorophenoxy)propyl)-5-benzofuranol (19b) can be produced in similar fashion. 19a: mp 125°-126° C; 19b: 116°-118° C.

| Micro analysis for 19a: | C | H |
|---|---|---|
| Calc'd: | 70.82 | 5.94 |
| Found: | 70.60 | 6.02 |
| Micro analysis for 19b: | C | H |
| Calc'd: | 66.23 | 5.69 |
| Found: | 66.29 | 5.80 |

EXAMPLE 20

2,3-dihydro-5-benzofuranol-6-carboxaldehyde methoxymethyl ether (20)

To a solution of 17 (34.50 g, 133 mmol) in dry tetrahydrofuran (325 mL) at −70° C. was added n-butyllithium (1.57 M in hexane, 95 mL, 149 mmol) dropwise such that the reaction temperature did not exceed −60° C. during the addition. The mixture was allowed to stir for 20 minutes at −70° C. then dry dimethylformamide (42 mL) was added dropwise (T$_{int}$ < −60° C.). The mixture was stirred for 1 hour then allowed to warm to 0° C. over 60 minutes. The mixture was poured into water (1000 mL) and after stirring for 1 hour extracted with ether (3×500 mL). The combined extracts were washed with water (500 mL), 20% NaCl (500 mL), dried (MgSO$_4$), and concentrated. Purification by preparative HPLC using 20% ethyl acetate in hexane as eluant gave 20 as a yellow solid. 20: mp 64°-65° C.

EXAMPLE 21

2,3-dihydro-5,6-benzofurandiol-5-methoxymethyl ether (21)

To a solution of 20 (1.50 g, 7.20 mmol) in methylene chloride (50 mL) was added p-nitro peroxybenzoic acid (2.64 g, 12.25 mmol) and the mixture refluxed under nitrogen for 24 hours. The reaction mixture was cooled, concentrated, and the residue taken up in ethyl acetate (100 mL). The solution was washed sequentially with 5% NaHCO$_3$ (3×50 mL), 5% Na$_2$SO$_3$ (2×50 mL), and 20% NaCl (50 mL), dried (Na$_2$SO$_4$), and concentrated to give a crude formate ester (1.42 g). The green oil was then taken up in methanol (50 mL) and saponified with aqueous KOH (0.430 g in 2 mL water). After one hour at room temperature, the methanol was removed and the residue diluted with water (50 mL). The aqueous solution was carefully acidified with 2N HCl then extracted with ethyl acetate (50 mL). The organic layer was washed with water (50 mL) and 5% Na$_2$SO$_3$ (2×50 mL), dried (Na$_2$SO$_4$), and concentrated to a dark oil. Flash chromatography using 20% ethyl acetate in hexane as eluant gave 21 as a pale oil which darkened on standing.

EXAMPLE 22

2,3-dihydro-6-butyloxy-5-benzofuranol 22a

To a mechanically stirred mixture of 21 (0.350 g, 1.68 mmol) and K$_2$CO$_3$ (2.20 g, 15.9 mmol) in acetone (60 ml) was added butyl bromide (1.40 g, 10.00 mmol) and the mixture heated to reflux for 16 hours. The reaction mixture was cooled, filtered, and the filtrate concentrated. Flash chromatography (10% ethyl acetate in hexane as eluant) gave the methoxy methyl ether (0.364 g) which was deprotected as a solution in methanol (30 mL) containing concentrated HCl (0.5 mL) at 55° C. The mixture was concentrated, diluted with water (50 ml) and extracted with ether (2×25 mL). The ether extracts were washed with 5% NaHCO3 (50 mL), dried (Na2SO4), and concentrated. Flash chromatography afforded 22a as a white solid. 2,3-Dihydro-6-(2-methoxyethoxy)-5-benzofuranol (22b); 2,3-dihydro-6-(2-phenylethoxy)-5-benzofuranol (22c) and 2,3-dihydro-6-(3-phenylpropoxy)-5-benzofuranol (23d) can be produced from 21 in similar fashion. 22a: mp 62°-63° C.; 22b: mp 60°-62° C.; 22c: mp 88°-90° C.; 22d: mp 110°-112° C.

| Micro analysis for 22a: | C | H |
|---|---|---|
| Calc'd: | 69.22 | 7.75 |
| Found: | 69.34 | 7.74 |
| Micro analysis for 22c: | C | H |
| Calc'd: | 74.98 | 6.29 |
| Found: | 74.79 | 6.14 |

EXAMPLE 23

2,3-dihydro-6-(3-phenoxypropoxy)-5-benzofuranol (23a)

To a suspension of sodium hydride (60% dispersion, 0.019 g, 0.47 mmol) in dry dimethyl formamide (4 mL) was added phenol (0.046 g, 0.47 mmol and the mixture allowed to stir until hydrogen evolution had ceased. A solution 27a (0.150 g, 0.47 mmol) in dry dimethylformamide (2 mL) was added dropwise and the mixture heated to 60° C. for 1 hour. The mixture was cooled, diluted with water (50 mL), and extracted with ethyl acetate (3×20 mL). The combined extracts were washed with water 3×20 mL), and 20% NaCl (20 mL), dried (Na2SO4), and concentrated. The residue was deprotected in methanol (20 mL) containing concentrated HCl (0.2 mL) at 55° C. for 1 hour. The methanol was removed by concentration, and the residue partitioned between water (50 mL) and ethyl acetate (25 mL). The aqueous layer was reextracted with ethyl acetate (2×25 mL), and the combined organic extracts washed sequentially with 5% NaHCO3 (25 mL), water (25 mL), and 25% NaCl (25 mL). The extracts were dried (Na2SO4), concentrated, and the crude product purified by flash chromatography using 10% ethyl acetate in hexane as eluant. Further purification was achieved by recrystallization from hexane to afford 23a (0.040 g, 30%). 2-(3-((2,3-Dihydro-5-hydroxy-6-benzofuranyl)oxy)propoxy)benzoic acid methyl ester methoxymethyl ether (23b) can be produced in similar fashion. 23a: mp 106°-107° C.

| Micro analysis for 23a: | C | H |
|---|---|---|
| Calc'd: | 70.22 | 6.41 |
| Found: | 70.44 | 6.07 |

EXAMPLE 24

2-(3-((2,3-dihydro-5-hydroxy-6-benzofuranyl)oxy)propoxy)benzoic acid methyl ester (24)

A solution of 23b (0.192 g, 0.26 mmol) was deprotected in methanol (10 mL) containing concentrated HCl (0.15 mL) as described above for 23a to afford 24. 24: mp 96°-97° C.

| Micro analysis for 24: | C | H |
|---|---|---|
| Calc'd: | 66.28 | 5.86 |
| Found: | 65.93 | 5.89 |

EXAMPLE 25

3-(3-((2,3-dihydro-5-hydroxy-6-benzofuranyl)oxy)propoxy)benzoic acid methyl ester methoxymethyl ether (25)

In a manner analogous to that described for 23a, methyl 3-hydroxybenzoate (0.240 g, 1.58 mmol) was alkylated with 27a (0.500 g, 1.58 mmol) to give as an oil.

EXAMPLE 26

3-(3-((2,3-dihydro-5-hydroxy-6-benzofuranyl)oxy)propoxy)benzoic acid methyl ester (26)

A solution of 25 (0.158 g, 0.40 mmol) was deprotected in methanol (15 mL) containing concentrated HCl (0.20 mL) as described above for 23a to afford 26. 26: mp 93°-° C.

| Micro analysis for 26: | C | H |
|---|---|---|
| Calc'd: | 65.42 | 5.92 |
| Found: | 65.17 | 5.91 |

EXAMPLE 27

2,3-dihydro-6-(3-bromopropoxy)-5-benzofuranol methoxymethyl ether (27a)

To a suspension of sodium hydride (60% dispersion, 0.728 g. 18.2 mmol) in dry dimethylformamide (20 mL) under nitrogen was added a solution of 21 (3.57 g, 18.2 mmol) in dimethylformamide (20 mL) dropwise over 30 minutes. After hydrogen evolution was complete the resulting solution of sodium alkoxide was added dropwise over 90 minutes to a solution of 1,3-dibromopropane (18.37 g, 91 mmol) in dimethylformamide (20 mL). The mixture was allowed to stir for 2 hours, then poured into water (200 mL), and extracted with ethyl acetate (4×30 mL). The combined extracts were washed with water (200 mL), dried (Na2SO4), and concentrated. Preparative HPLC using 15% ethyl acetate as eluant gave 27a as an oil.

In a manner analogous to that described for 23a, methyl 4-hydroxybenzoate (0.240 g, 1.58 mmol) was alkylated with 27a (0.500 g, 1.58 mmol) to give 27b as an oil.

EXAMPLE 28

4-(3-((2,3-dihydro-5-hydroxy-6-benzofuranyl)oxy)propoxy)benzoic acid methyl ester (28)

A solution of 27b 0.580 g, 1.69 mmol) was deprotected in methanol (30 mL) containing concentrated HCl 0.25 mL) as described above for 23a to afford 28. 28; mp 133°-135° C.

| Micro analysis for 28: | C | H |
|---|---|---|
| Calc'd: | 66.28 | 5.86 |
| Found: | 66.18 | 5.89 |

EXAMPLE 29

4-(3-((2,3-dihydro-5-hydroxy-6-benzofuranyl)oxy)-propoxy)benzeneacetic acid methyl ester methoxymethyl ether (29)

In a manner analogous to that described for 23a, methyl 4-hydroxyphenyl acetate (0.236 g, 1.42 mmol) was alkylated with 27a (0.450 g, 1.42 mmol) to give crude 29 as an oil.

EXAMPLE 30

4-(3-((2,3-dihydro-5-hydroxy-6-benzofuranyl)oxy)-propoxy)benzeneacetic acid methyl ester (30)

A solution of 29 (0.250 g, 0.62 mmol) was deprotected in methanol (25 mL) containing concentrated HCl 0.20 mL) as described above for 23a to afford 30. 30: mp 108°–110° C.

| Micro analysis for 30: | C | H |
|---|---|---|
| Calc'd: | 67.04 | 6.19 |
| Found: | 67.04 | 6.29 |

EXAMPLE 31

2,3-dihydro-5-hydroxybenzofuran-6-carboxylic acid ethyl ester methoxymethyl ether (31)

A solution of 17 (58.8 g, 227 mmol) in tetrahydrofuran (250 mL) was cooled with a dry ice acetone bath to −60° C. then a solution of n butyllithium (2.5 M in hexanes, 250 mmol) was added dropwise via a cannula. The reaction mixture was not allowed to exceed −50° C. during the addition. Upon completion of the addition the mixture was allowed to stir for 30 minutes with dry ice acetone cooling then cannulated with a Flex-Needle into a dry ice/acetone cooled solution of ethyl chloroformate (24 mL, 27.1 g, 250 mmol) in tetrahydrofuran (200 mL) over 90 minutes. During the addition the reaction temperature was maintained at −65° C. Upon completion of the addition the cooling bath was removed and the reaction mixture allowed to warm to room temperature over one hour. The reaction was then worked up by pouring into 5% NaHCO$_3$ (1600 mL) and the resulting mixture saturated with NaCl. Ether (500 mL) was added and the layers separated. The aqueous layer was reextracted with ether (500 mL) and the combined organic layers dried with MgSO$_4$ and concentrated to afford 31 as an oil which was used without further purification.

EXAMPLE 32

2,3-Dihydro6-(1-methyl-1-hydroxyethyl)-5-benzofuranol methoxymethyl ether

A solution of methyllithium (1.4 M in ether, 21.4 mL, 30 mmol) was cooled to −70° C. under nitrogen then a solution of 31 (2.50 g, 10 mmol) in ether (6 mL) was added dropwise via syringe at a rate such that the internal temperature did not exceed −60° C. Upon completion of the addition the mixture was stirred at −78° C. for 45 minutes then allowed to warm to 0° C. slowly. The reaction was worked up by pouring into water (50 mL) and separating the layers. The aqueous layer was reextracted with an additional portion of ether (50 mL) and the combined organic extracts washed with 20% NaCl (50 mL), dried (MgSO$_4$) and concentrated. The resulting crude product began to slowly crystallize. Trituration with hexane afforded 32 as a white solid.

EXAMPLE 33

2,3-Dihydro-6-(1-methylethyl)-5-benzofuranol

An oven dried 50 mL 3 neck flask equipped with a dry ice acetone condenser and a gas inlet was flushed with nitrogen then anhydrous ammonia (5 mL) was condensed in. Dry tetrahydrofuran (4 mL) was added followed by lithium wire (0.041 g, 5.91 mmol, in 3 pieces). A deep blue color was immediately observed. A solution of 32 (0.412 g, 1.73 mmol) in dry tetrahydrofuran (4 mL) was then added dropwise in portions. Whenever the blue color was quenched the addition was suspended until the blue color returned. The total addition time was about 20 minutes. Upon completion of the addition the blue color returned and the mixture was allowed to stir at refluxing ammonia temperature for 10 minutes. The reaction was quenched by the portionwise addition of ammonium chloride (0.471 g) and the ammonia allowed to evaporate. The resulting mixture was partitioned between ether (50 mL) and 10% NaCl (100 mL). The aqueous fraction was reextracted with an additional portion of ether and the combined extracts dried (MgSO$_4$) and concentrated to a pale oil (0.320 g). Chromatography through a short column of flash silica gel using 7% ethyl acetate in hexane as eluant afforded a colorless liquid (0.256 g). This material was deprotected in methanol (10 mL) containing concentrated HCl (0.20 mL) at 55° C. to give 33 as a white solid. Recrystallization from hexane afforded an analytical sample.

EXAMPLE 34

4-Methylbenzofuran-5-carboxaldehyde (34)

To a suspension of dichlorodicyano 1,4-benzoquinone (60.8 g, 267 mmol) in dioxane (220 mL) was added a solution of compound 45 (4-methyl-6,7-dihydrobenzofuran-5-carboxaldehyde) (36.82 g, 227 mmol) in dioxane (220 mL) over 2.5 hours. The mixture was allowed to stir an additional 20 minutes then diluted with methylene chloride (450 mL). The mixture was filtered through celite to remove the hydroquinone and the filter cake was washed with an additional portion of methylene chloride (450 mL). The filtrate was concentrated and chromatographed through a large (9 cm diameter) column of flash silica gel. Elution with 10% ethyl acetate in hexane gave 34 as a pale peach solid.

EXAMPLE 35

4-Methyl-5-benzofuranol (35)

To a solution of 34 (33.06 g, 206 mmol) in methylene chloride (580 mL) was added 80% m chloroperbenzoic acid (52.0 g, 211 mmol) and the mixture heated at reflux for 17 hours. The reaction mixture was allowed to cool, diluted with ethyl acetate (580 mL) and extracted with 5% NaHCO$_3$ (2×725 mL). The aqueous layers were back extracted with additional portions of ethyl acetate (290 mL) and the combined organic layers dried (MgSO$_4$) and concentrated. The resulting yellow oil (47 ) was taken up in methanol (700 mL) and 2.5N NaOH (185 mL, 462 mmol) was added. The mixture was stirred at room temperature for 20 minutes, cooled with an ice bath, and acidified with 2N HCl (810 mL). The resulting mixture was saturated with NaCl and extracted with ethyl acetate (3×1200 mL). The combined extracts were washed with 20% NaCl (2×900 mL), dried (MgSO$_4$) and concentrated. The resulting dark oil (51 g) was chromatographed through a large (9 cm diameter) column of flash silica gel. Elution with 12.5% ethyl acetate in hexane afforded 36 as an off white solid.

EXAMPLE 36

2,3-dihydro-4-methyl-5-benzofuranol (36)

A solution of 35 (1.86 g, 12.6 mmol) in absolute ethanol (50 mL) was hydrogenated over 10% palladium on carbon catalyst (0.10 g) at 3 atmospheres pressure. After the required amount of hydrogen had been taken up (overnight) the catalyst was removed by filtration and washed with an additional portion of absolute ethanol (20 mL). The combined filtrate and washings were concentrated to a white crystalline solid (1.88 g). Recrystallization from toluene gave 36.

EXAMPLE 37

2,3-dihydro-4-methyl-6-(propen-3-yl) 5-benzofuranol (37)

In a manner analogous to that described above for 2a, 36 (1.00 g, 6.66 mmol) was alkylated with allyl bromide (1.76 g, 14.6 mmol) to give the allyl ether. The allyl ether (1.23 g) was thermally rearranged in 1,2-dichlorobenzene (8 mL) at 190° C. for 3.5 hours to afford, after chromatographic purification, compound 37. Recrystallization from hexane gave an analytical sample. 37: mp 60°–61° C.

| Micro analysis for 37: | C | H |
|---|---|---|
| Calc'd: | 75.76 | 7.42 |
| Found: | 76.00 | 7.57 |

EXAMPLE 38

2,3-dihydro-4-methyl-6-propyl-5-benzofuranol (38)

A solution of 37 (0.500 g, 2.63 mmol) in absolute ethanol (25 mL) was hydrogenated over 5% palladium on carbon (0.060 g) at 3 atmospheres pressure. After hydrogen uptake was complete (30 minutes) the catalyst was removed by filtration through celite. The filter cake was washed with an additional portion of ethanol (30 mL) and the combined filtrate and washings concentrated to a white crystalline solid. Recrystallization from hexane gave 38. 38: mp 72°–73° C.

| Micro analysis for 38: | C | H |
|---|---|---|
| Calc'd: | 74.96 | 8.39 |
| Found: | 75.00 | 8.61 |

EXAMPLE 39

2,3-dihydro-4-methyl-6-(3-(phenylthio)propyl)5-benzofuranol (39)

A mixture of 37 (0.150 g, 0.79 mmol), thiophenol (0.5 mL, 0.54 g, 4.88 mmol), and AIBN (0.025 g) was heated to 90° for 2.5 hours then 100° C. for 4 hours. The reaction mixture after cooling was purified by flash chromatography using 0 to 10% ethyl acetate in hexane as eluant. Recrystallization from hexane containing a small amount of toluene afforded 40 as fluffy white needles. 39: mp 80°–81° C.

EXAMPLE 40

2,3-dihydro4-bromo-6-propyl-5-benzofuranol (40)

To a cooled (10° C.) solution of 3a (5.00 g, 28.1 mmol) in methylene chloride (50 mL) was added dropwise a solution of bromine (4.75 g, 29.72 mmol) in methylene chloride (50 mL) and the mixture allowed to stir for 1 hour. The reaction mixture was then poured into 5% NaHCO$_3$(100 mL). The organic layer was separated and the aqueous layer reextracted with an additional portion of methylene chloride. The combined organic layers were washed sequentially with 5% NaHSO$_3$ (100 mL) and 20% NaCl 100 mL) then dried (Na$_2$SO$_4$), and concentrated. Preparative HPLC using 3% ethyl acetate in hexane as eluant gave 40 as an oil which solidified on standing in the cold. 40: mp 42°–43° C.

| Micro analysis for 40: | C | H | Br |
|---|---|---|---|
| Calc'd: | 51.38 | 5.10 | 31.08 |
| Found: | 51.11 | 5.06 | 31.39 |

EXAMPLE 41

2,3-dihydro4-t-butyl-5-benzofuranol (41a) and 2,3-dihydro-4-t-butyl-6-(propen-3-yl)-5-benzofuranol (41b)

A 2000-mL 3-neck flask fitted with nitrogen inlet, low temperature thermometer, and 500-mL pressure equilibrated dropping funnel is flame dried and charged with dry hexane (freshly distilled from calcium hydride, 200 mL). The flask is cooled with an external dry ice-/acetone bath then tert-butyl-lithium (1.7 M in pentane, 200 mL, 340 mmol) is added via double ended needle transfer. The resulting solution is cooled to −65° C. internal temperature then a solution of 43 (40.00 g, 294 mmol) in a mixture of ether (100 mL) and hexane (300 mL) is added dropwise over 1 hour at a rate such that the reaction temperature does not exceed −55° C. Upon completion of the addition the reaction mixture is stirred with dry ice/acetone cooling for 10 minutes, the cooling bath is removed and the reaction allowed to gradually warm. After 1 hour the temperature reaches about 5° C. The reaction is quenched by dropwise addition of water (40 mL), followed immediately by 2N HCl (200 mL) and tetrahydrofuran (200 mL). The reaction mixture is then poured into a 4000-mL Erlenmeyer flask containing 2N HCl (200 mL) and the resulting mixture diluted to a total volume of 2800 mL with tetrahydrofuran. The elimination is allowed to proceed for 2.5 hours then 20% NaCl (500 mL) was added and the layers separated. The aqueous layer was reextracted with ether (500 mL) and the combined organic layers washed with 20% NaCl (500 mL), dried (Na$_2$SO$_4$) and concentrated to a reddish oil (48.7 g) which is distilled. The total distillate is chromatographed (Water Prep 500A) using hexane as eluant to afford 4-tert-butyl-6,7-dihydrobenzofuran as a colorless liquid.

A flame-dried 2000-mL 3-neck flask fitted with a 250-mL pressure equilibrated dropping funnel, and internal thermometer, and nitrogen inlet is charged with a solution of 4-tert-butyl-6,7 dihydrobenzofuran (24.26 g, 137.8 mmol) in dry tetrahydrofuran (300 mL). The solution is cooled to 4° C. then a solution of borane 1M in tetrahydrofuran, 142 mL) is added dropwise over 20 minutes such that the internal temperature does not exceed 5° C. during the addition. The cooling bath is removed and the reaction mixture is allowed to warm to room temperature and stir for 2.5 hours. The reaction is then quenched by the dropwise addition of water (9.5 mL) followed (after hydrogen evolution was complete) by the addition of 2.5N NaOH (280 mL). Hydrogen peroxide (30% aqueous solution, 16 mL) is carefully added dropwise such that the reaction temperature is about 45° C. upon completion of the addition. An oil bath is added and the reaction mixture maintained at 45°–50° C. for one hour. The reaction mixture is allowed to cool, then diluted with 20% NaCl (500 mL). The layers are separated and the aqueous layer extracted with an additional portion of tetrahydrofuran (300 mL). The combined organic extracts are washed with 20% NaCl (500 mL), dried (MgSO4), and concentrated. Trituration with hexane afforded trans-4-tert butyl-4,5,6,7-tetrahydro-5-benzofuranol.

A 1000-mL 3-neck flask fitted with a 250-mL dropping funnel, mechanical stirring, and an internal thermometer is flame dried then charged with a solution of oxalyl chloride (13.4 mL, 19.5 g, 130 mmol) in methylene chloride (240 mL) and cooled to −78° C. with a dry ice/acetone bath. A solution of dimethyl sulfoxide (21.3 mL, 23.5 g, 300 mmol) in methylene chloride (55 mL) is added dropwise over 15 minutes while maintaining the reaction temperature below −70° C. The mixture is allowed to stir for an additional 20 minutes then a solution of trans-4-butyl-4,5,6,7-tetrahydro-5-benzofuranol (21.85 g, 112.5 mmol) is added dropwise over about 15 minutes. The mixture is stirred at −78° C. for one hour, then triethylamine (freshly distilled from CaH2, 87 mL, 625 mmol) is added dropwise over about 20 minutes. During the addition the reaction temperature increased to −50° C. The cooling bath is removed and the white suspension allowed to warm to room temperature over one hour. The reaction is then poured into water (900 mL) and the layers separated. The aqueous layer is reextracted with methylene chloride (300 mL) and the combined organic layers extracted sequentially with 2N HCl (500 mL), 5% NaHCO3 (1000 mL) and 20% NaCl (1000 mL), dried (MgSO4), and concentrated to a dark oil. Chromotography (Waters Prep 500A) using 10% ethyl acetate in hexane as eluant affords 4-tert-butyl-4,5,6,7-tetrahydro -5-benzofuranone as a pale yellow oil which slowly darkens upon prolonged standing.

A mixture of 4 tert butyl-4,5,6,7 tetrahydro-5-benzofuranone (1.00 g, 5.2 mmol) and sulfur (0.167 g, 1 equivalent) in a sealable tube is flushed with nitrogen, sealed and heated to 225° C. for 30 minutes. An additional portion of sulfur (0.030 g) is then added and the mixture heated an additional 15 minutes. After cooling the total reaction mixture is taken up in a small portion of methylene chloride and applied directly to a flash silica gel column. Elution with 5% ethyl acetate in hexane gives 4-tert-butyl5-benzofuranol.

To a solution of 4-tert butyl-5-benzofuranol (0,660 g, 3.47 mmol) 41a in acetic acid (20 mL) is added 10% palladium on carbon (0.130 ) and the mixture hydrogenated overnight at 40 psi. The reaction mixture is taken up in ether (25 mL) and filtered through a bed of Celite to remove the catalyst. The filtrate and washing are diluted with water (100 mL) and ether (50 mL) and the layers separated. The aqueous layer is washed with an additional portion of ether (50 mL) and the combined extracts washed sequentially with 5% NaHCO3 (3×50 mL), water (50 mL), and 20% NaCl (50 mL) then dried (MgSO4) and concentrated. Purification by flash chromatography using 5% ethyl acetate in hexane as eluant gives 4-tert-butyl-2,3-dihydro-5-benzofuranol.

To a suspension of sodium hydride (60% dispersion in mineral oil, 0.160 g, 3.99 mmol) in dry dimethylformamide (4.5 mL) is added a solution of 4-tert-butyl-2,3-dihydro-5-benzofuranol (0.511 g, 2.66 mmol) in dimethylformamide (4 mL). After hydrogen evolution has ceased a solution of allyl bromide (0.483 g, 3.99 mmol) in dimethylformamide (4 mL) is added and the mixture heated to 50° C. under nitrogen. After 1 hour the reaction mixture was poured into 20% NaCl (125 mL) and extracted with ether (0.656 g). This material is taken up in 1,3-dichlorobenzene (6 mL) and heated to reflux under nitrogen for 16 hours. Purification by flash chromatography using 2% ethyl acetate in hexane as eluant gives 41b (0.327 g, 53%) as a pale yellow solid. 41b: mp 92°–95° C.

EXAMPLE 42

2,3-dihydro-4-t-butyl-6-propyl-5-benzofuranol (42)

To a solution of 41 (0.230 g, 0.99 mmol) in absolute ethanol 12 mL) was added 10% palladium on carbon (0.020 g) and the solution hydrogenated at 3 atmospheres pressure. After 30 minutes the catalyst was removed by filtration through celite and the filter cake washed with a small portion of ethanol. The combined filtrate and washings were concentrated to afford a crude product 0.210 g). Recrystallization from aqueous ethanol gave 42 as a white solid. 42: mp 129°–130° C.

While presently preferred embodiments of the invention have been described in detail for purposes of disclosure, numerous alternatives will readily suggest themselves to those skilled in the art and are encompassed within the principles of the invention and the scope of the appended claims.

What is claimed is:

1. A compound according to Formula 1 or a pharmaceutically acceptable salt thereof

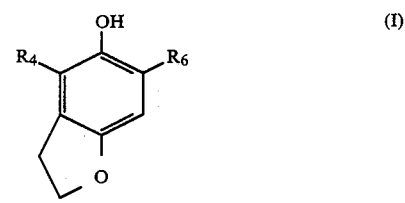

wherein:
$R_4$ is hydrogen.
$R_6$ is
(a) $C_{3-4}$ alkenyl;
(b) substituted $C_{3-4}$ alkyl wherein the substituent is:
(1) phenylthio;
(2) pyridylmethylthio;
(3) hydroxy;
(4) cyano;
(5) phenoxy;
(6) phenylamino;
(7) hydroxy $C_{1-6}$alkyl phenoxy;
(8) $C_{1-6}$ alkyl phenoxy; or
(9) halophenoxy;
(c) phenylthio;
(d) phenyl $C_{1-6}$ alkylthio;
(e) pyridylthio;
(f) phenoxy;
(g) $C_{2-4}$ alkoxy; or (h) substituted $C_{2-4}$ alkoxy wherein the substituent is:
  (1) methoxy;
  (2) phenyl;
  (3) phenoxy;
  (4) carboxy $C_{1-6}$ alkylphenoxy, or their $C_{2-4}$ alkyl esters; or
  (5) carboxyphenoxy, or their $C_{1-6}$ alkylesters.

2. A compound according to claim 1 wherein:
$R_6$ is
  (a) $C_{3-4}$ alkenyl;
  (b) substituted $C_{3-4}$ alkyl wherein the substituent is:
    (1) phenylthio;
    (2) pyridylmethylthio;
    (3) phenoxy;
    (4) hydroxy $C_{2-4}$ alkylphenoxy;
    (5) $C_{2-4}$ alkylphenoxy
    (6) halophenoxy;
  (c) phenylthio;
  (d) phenyl $C_{1-6}$ alkylthio;
  (e) $C_{2-4}$ alkoxy;
  (f) substituted $C_{2-4}$ alkoxy wherein the substituent is:
    (1) phenyl;
    (2) phenoxy; or
    (3) carboxy $C_{1-6}$ alkylphenoxy; or their $C_2$-$C_4$ alkyl esters.

3. A compound according to claim 2 selected from the group consisting of:
  (a) 2,3-dihydro-6-(propen-3-yl)-5-benzofuranol;
  (b) 2,3-dihydro-6-(3-pyridylmethylthio)propyl)-5-benzofuranol;
  (c) N-Phenyl-3-(2,3-dihydro-5-(benzofuranol-6-yl)propylamine;
  (d) 2,3-dihydro-6-(3-(3-(2-hydroxyethyl)-phenoxy)-propyl)-5-benzofuranol;
  (e) 2,3-dihydro-6-phenylthio-5-benzofuranol;
  (f) 2,3-dihydro-6-phenylmethylthio-5-benzofuranol;
  (g) 2,3-dihydro-6-butyloxy-5-benzofuranol;
  (h) 2,3-dihydro-6-(2-phenylethoxy)-5benzofuranol; or
  (i) 2,3-dihydro-6-(3-phenoxypropoxy)-5-benzofuranol.

4. A compound selected from the group consisting of:
  (a) 2,3-dihydro-6-(3-(phenylthio)propyl)-5-benzofuranol;
  (b) 2,3-dihydro-6-(3-phenoxypropyl)-5-benzofuranol;
  (c) 2,3-dihydro-6-(3-(4-(2-hydroxyethyl)-phenoxy)-propyl)-5-benzofuranol;
  (d) 2,3-dihydro-6-(3-(3-(2-hydroxyethyl)-phenoxy)-propyl)-5-benzofuranol;
  (e) 2,3-dihydro-6-(3-(4-propylphenoxy)propyl)-5-benzofuranol;
  (f) 2,3-dihydro-6-(2-phenylethyl)thio-5-benzofuranol;
  (g) 2,3-dihydro-6-(3-phenylpropyl)thio-5-benzofuranol;
  (h) 2,3-dihydro-6-(3-(4-fluorophenoxy)-propyl)-5-benzofuranol;
  (i) 2,3-dihydro-6-(3-(4-chlorophenoxy)-propyl)-5-benzofuranol;
  (j) 2,3-dihydro-6-(3-phenylpropoxy)-5-benzofuranol;
  (k) 3-(3-((2,3-dihydro-5-hydroxy-6-benzofuranyl)oxy)propoxy)benzoic acid methyl ester;
  (l) 4-(3-((2,3-dihydro-5-hydroxy-6-benzofuranyl)oxy)propoxy)benzoic acid methyl ester; or
  (m) 4-(3-((2,3-dihydro-5-hydroxy-6-benzofuranyl)oxy)propoxy)benzeneacetic acid methyl ester;
or pharmaceutically acceptable salts thereof.

5. A pharmaceutical composition for treating leukotriene medicated diseases comprising a pharmaceutical carrier and a non-toxic effective amount of a compound, according to claim 1.

6. A pharmaceutical composition for treating leukotriene mediated diseases comprising a pharmaceutical carrier and a non-toxic effective amount of a compound, according to claim 4.

7. A pharmaceutical composition according to claim 5 wherein the compound is selected from the group consisting of:
  (a) 2,3-dihydro-6-(propen-3-yl)-5-benzofuranol;
  (b) 2,3-dihydro-6-(3-(3-pyridylmethylthio)propyl)-5-benzofuranol;
  (c) N-Phenyl-3-(2,3-dihydro-5-(benzofuranol-6-yl)propyl amine;
  (d) 2,3-dihydro-6-(3-(2-hydroxyethyl)-phenoxy)-propyl)-5-benzofuranol;
  (e) 2,3-dihydro-6-phenylthio-5-benzofuranol;
  (f) 2,3-dihydro-6-phenylmethylthio-5-benzofuranol;
  (g) 2,3-dihydro-6-butyloxy-5-benzofuranol;
  (h) 2,3-dihydro-6-(2-phenylethoxy)-5-benzofuranol; or
  (i) 2,3-dihydro-6-(3-phenoxypropoxy)-5-benzofuranol; or
or a pharmaceutically acceptable salt thereof.

8. A method of treating leukotriene mediated diseases comprising the administration to a subject in need of such treatment a therapeutically effective amount of a compound according to claim 1.

9. A method of treating inflammation according to claim 8 wherein the compound is selected from the group consisting of:
  (a) 2,3-dihydro-6-(propen-3-yl)-5-benzofuranol;
  (b) 2,3-dihydro-6-(3-(3-pyridylmethylthio)propyl)-5-benzofuranol;
  (c) N-Phenyl-3-(2,3-dihydro-5-(benzofuranol-6-yl)propyl amine;
  (d) 2,3-dihydro-6-(3-(2-hydroxyethyl)-phenoxy)propyl-5-benzofuranol;
  (e) 2,3-dihydro-6-phenylthio-5-benzofuranol;
  (f) 2,3-dihydro-6-phenylmethylthio-5-benzofuranol;
  (g) 2,3-dihydro-6-butyloxy-5-benzofuranol;
  (h) 2,3-dihydro-6-(2-phenylethoxy)-5-benzofuranol;
  (i) 2,3-dihydro-6-(3-phenoxypropoxy)-5-benzofuranol;
  (j) 2,3-dihydro-4-(3-phenylthio)propyl)-5-benzofuranol; or
  (k) 2,3-dihydro-4-(3-phenoxypropyl)-5-benzofuranol;
or pharmaceutically acceptable salts thereof.

10. A method of treating leukotriene mediated diseases comprising the administration to a subject in need of such treatment a therapeutically effective amount of a compound according to claim 4.

* * * * *